(12) United States Patent
Ishida et al.

(10) Patent No.: US 8,735,446 B2
(45) Date of Patent: May 27, 2014

(54) VANILLIN ACETALS AND SENSORY STIMULANT COMPOSITION CONTAINING THE SAME

(75) Inventors: Kenya Ishida, Kanagawa (JP); Takashi Aida, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 71 days.

(21) Appl. No.: 13/467,770

(22) Filed: May 9, 2012

(65) Prior Publication Data

US 2012/0219512 A1    Aug. 30, 2012

Related U.S. Application Data

(62) Division of application No. 11/988,237, filed as application No. PCT/JP2006/313799 on Jul. 5, 2006, now Pat. No. 8,236,970.

(30) Foreign Application Priority Data

Jul. 6, 2005  (JP) .................................. 2005-197205

(51) Int. Cl.
    *A61K 31/335*    (2006.01)
(52) U.S. Cl.
    USPC ......................................................... 514/463

(58) Field of Classification Search
    USPC ......................................................... 514/463
    See application file for complete search history.

(56) References Cited

U.S. PATENT DOCUMENTS

| | | |
|---|---|---|
| 5,144,048 A | 9/1992 | Christenson et al. |
| 5,545,424 A | 8/1996 | Nakatsu et al. |
| 5,626,852 A | 5/1997 | Suffis et al. |
| 5,753,609 A | 5/1998 | Nakatsu et al. |

FOREIGN PATENT DOCUMENTS

| | | |
|---|---|---|
| EP | 1 121 927 A2 | 8/2001 |
| JP | 57-9729 | 1/1982 |
| JP | 57-82308 | 5/1982 |
| JP | 8-225564 | 9/1996 |
| JP | 2001-2673 | 1/2001 |
| JP | 2003-137758 | 5/2003 |
| WO | WO 2005/115325 A1 | 12/2005 |

*Primary Examiner* — Kevin E Weddington
(74) *Attorney, Agent, or Firm* — McDermott Will & Emery LLP

(57) ABSTRACT

The invention relates to a sensory stimulant composition containing one or more of vanillin acetals represented by the general formula (1), and a flavor and fragrance composition, a beverage or food product, a fragrance or cosmetic product, a daily utensil product, an oral composition, or a pharmaceutical product containing the sensory stimulant composition with a warming sensation agent or cooling sensation substance, if necessary. Vanillin acetals represented by the general formula (1) show an excellent pungent and/or warming sensation effect and a cooling sensation-emphasizing effect.

9 Claims, No Drawings

VANILLIN ACETALS AND SENSORY STIMULANT COMPOSITION CONTAINING THE SAME

RELATED APPLICATIONS

This application is a Divisional of U.S. application Ser. No. 11/988,237, filed on Jan. 3, 2008, now U.S. Pat. No. 8,236,970 which is the U.S. National Phase under 35 U.S.C. §371 of International Application No. PCT/JP2006/313799, filed on Jul. 5, 2006, which in turn claims the benefit of Japanese Application No. 2005-197205, filed on Jul. 6, 2005, the disclosures of which Applications are incorporated by reference herein.

TECHNICAL FIELD

The invention relates to vanillin acetals and a sensory stimulant composition containing the vanillin acetals. Further, the invention relates to a flavor and fragrance composition, a beverage or food product, a fragrance or cosmetic product, a daily utensil product, an oral composition, or a pharmaceutical product containing the sensory stimulant composition, and a method of producing the same.

BACKGROUND ART

Conventionally, substances imparting stimulating sensory feeling (pungent sensation) and warming sensory feeling (warming sensation) to the skin, oral cavity, nose and throat of a person, so-called sensory stimulants, have been used for toothpastes, confectionery (e.g. chewing gum and candies), tobacco, cataplasm products, bath agents, and cosmetics. As a compound which imparts such pungent and warming sensations, there has been known a vanillyl alcohol derivative (hereinafter, abbreviated as VE in some cases) represented by the following general formula (2):

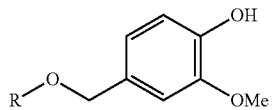

(2)

wherein R represents an alkyl group having 1 to 6 carbon atoms, and 'Me' represents a methyl group, hereinafter the same. In addition, Japanese Patent Application Laid-Open No. 57-009729 (JP-A-57-009729) discloses that the compound has a strong pungent and/or warming sensation effect and JP-A-57-082308 discloses that the compound emphasizes a cooling sensation effect of menthol.

Although the VEs have the strong pungent and/or warming sensation effect, they also have problems that they are easy to be colored under the basic condition and that coloration and taste alteration are easily caused with the lapse of time. Therefore, in the addition of VE to commercial products, the amount of VE and the kind of product to be added are limited. Further, since the complicated reaction steps such as reduction and etherification of vanillin are needed in the production of VE, it has been desired to provide a sensory stimulant easy to produce and excellent in the effect.

On the other hand, vanillin propylene glycol acetal has been conventionally known as a vanillin acetal compound (refer to JP-A-2003-137758). However, it is simply exemplified as a fragrance for hair treatment cosmetics, and the sensory stimulating effect thereof has been unknown. Further, although it has been known that a vanillin acetal compound, vanillin 2,3-butanediol acetal, is used as a fragrance agent (refer to JP-A-2001-002673), a sensory stimulating effect of this compound has also been unknown.

Further, JP-A-8-225564 discloses, as a sensory stimulant, 4-(l-menthoxymethyl)-2-phenyl-1,3-dioxolane and its derivatives represented by the following general formula (3):

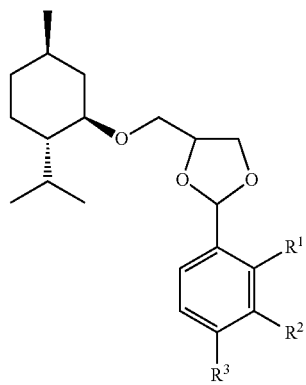

(3)

wherein $R^1$ represents a hydrogen atom, a hydroxyl group, or a lower alkoxy group; $R^2$ and $R^3$ may be same or different and independently represent a hydrogen atom, a hydroxyl group, or a lower alkoxy group, or $R^2$ and $R^3$ are bonded to each other to form a methylenedioxy group. However, their effect is not sufficient, and therefore it has been desired to obtain a compound having a more excellent pungent and/or warming sensation effect and cooling sensation-emphasizing effect.

As described above, sensory stimulants having the pungent and/or warming sensation effect and additionally the cooling sensation-emphasizing effect have been known conventionally. However, these conventionally known sensory stimulants have problems, that is, they easily cause coloration and taste alteration with the lapse of time or in accordance with the use conditions; the production process includes the complicated reaction steps; the pungent and/or warming sensation effect and a lasting effect thereof are insufficient; and the cooling sensation-emphasizing effect is insufficient. It has been desired to solve these problems.

DISCLOSURE OF INVENTION

Accordingly, an object of the invention is to provide a sensory stimulant free from the conventional problems above, and a sensory stimulant composition containing the sensory stimulant.

More specifically, the object of the invention is to provide a sensory stimulant having an excellent pungent and/or warming sensation effect and excellent in stability and cooling sensation-emphasizing effect, and a sensory stimulant composition containing the sensory stimulant as well as to provide a flavor and fragrance composition, a beverage or food product, a fragrance or cosmetic product, a daily utensil product, an oral composition, or a pharmaceutical product containing the sensory stimulant or the sensory stimulant composition containing the sensory stimulant or the sensory stimulant composition, and a method of producing the same.

Another object of the invention is to provide a novel compound preferable as a sensory stimulant.

The inventors of the invention have made various investigations of the pungent and/or warming sensation effect of various kinds of compounds derived from vanillin in order to solve the above-mentioned problems. As a result, they have found that vanillin acetals represented by the following general formula (1) have a strong pungent and/or warming sensation effect and an excellent lasting effect thereof, and therefore they are useful as a sensory stimulant. In addition, they also have found that in the case where VEs are added to a cooling sensation substance, they impart a cooling sensation-emphasizing effect; and that they are synthesized easily and the obtained compounds are excellent in stability. Consequently, the invention has been accomplished based on the findings.

That is, the invention is as described in items 1 to 18 below.

1. A sensory stimulant composition containing one or more of vanillin acetals represented by the general formula (1):

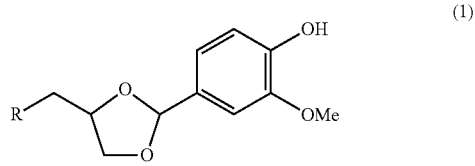

wherein R represents a hydrogen atom, a straight chain or branched alkyl group having 1 to 9 carbon atoms, or a straight chain or branched alkoxy group having 1 to 8 carbon atoms.

2. The sensory stimulant composition according to the item 1 above, wherein the sensory stimulant composition is a pungent agent composition.

3. The sensory stimulant composition according to item 1 above, wherein the sensory stimulant composition is a warming sensation agent composition.

4. The sensory stimulant composition according to any one of items 1 to 3 above, which further comprises one or more kinds of components selected from cooling sensation substances.

5. The sensory stimulant composition according to item 4 above, wherein the cooling sensation substances are menthol, menthone, camphor, pulegol, isopulegol, cineole, mint oil, peppermint oil, spearmint oil, eucalyptus oil, 3-l-menthoxypropane-1,2-diol, N-alkyl-p-menthane-3-carboxamide, 3-l-menthoxy-2-methylpropane-1,2-diol, p-menthane-3,8-diol, 2-l-menthoxyethan-1-ol, 3-l-menthoxypropan-1-ol, 4-l-menthoxybutan-1-ol, menthyl 3-hydroxybutanate, menthyl lactate, menthone glycerin ketal, 2-(2-l-menthyloxyethyl)-ethanol, menthyl glyoxylate, 1-(2-hydroxy-4-methylcyclohexyl)ethanone, N-methyl-2,2-isopropylmethyl-3-methylbutanamide, menthyl 2-pyrrolidone-5-carboxylate, monomenthyl succinate, alkali metal salts of monomenthyl succinate, alkaline earth metal salts of monomenthyl succinate, monomenthyl glutarate, alkali metal salts of monomenthyl glutarate, alkali earth metal salts of monomenthyl glutarate, N-[[5-methyl-2-(1-methylethyl)cyclohexyl]carbonyl] glycine, p-menthane-3-carboxylic acid glycerol ester, Menthol propylene glycol carbonate, Menthol ethylene glycol carbonate, and 6-isopropyl-3,9-dimethyl-1,4-dioxaspiro [4.5]decan-2-one.

6. The sensory stimulant composition according to any one of items 1 to 5 above, further comprising one or more kinds of components selected from sensory stimulants consisting of a compound or compounds not included in the vanillin acetals represented by the general formula (1).

7. The sensory stimulant composition according to item 6 above, wherein the sensory stimulants consisting of a compound or compounds not included in the vanillin acetals represented by the general formula (1) are one or more compounds selected from vanillyl ethyl ether, vanillyl propyl ether, capsaicine, gingerol, vanillyl butyl ether, vanillyl butyl ether acetate, 4-(l-menthoxymethyl)-2-phenyl-1,3-dioxolan, 4-(l-menthoxymethyl)-2-(3',4'-dihydroxyphenyl)-1,3-dioxolan, 4-(l-menthoxymethyl)-2-(2'-hydroxy-3'-methoxyphenyl)-1,3-dioxolan, 4-(l-menthoxymethyl)-2-(4'-methoxyphenyl)-1,3-dioxolan, 4-(l-menthoxymethyl)-2-(3',4'-methylenedioxy-phenyl)-1,3-dioxolan, 4-(l-menthoxymethyl)-2-(3'-methoxy-4'-hydroxyphenyl)-1,3-dioxolan, red pepper oil, red pepper oleoresin, ginger oleoresin, nonylic acid vanillyl amide, jamboo oleoresin, *Zanthoxylum piperitum* extract, sanshool I, sanshool II, sanshoamide, black pepper extract, chavicine, pipeline, and spilanthole.

8. A flavor and fragrance composition containing 0.0001 to 90% by weight of the sensory stimulant composition according to any one of items 1 to 7 above.

9. A beverage or food product, a fragrance or cosmetic product, a daily utensil product, an oral composition, or a pharmaceutical product containing 0.0001 to 20% by weight of the sensory stimulant composition according to any one of items 1 to 7 above.

10. A method of producing a flavor and fragrance composition, a beverage or food product, a fragrance or cosmetic product, a daily utensil product, an oral composition, or a pharmaceutical product, comprising adding the sensory stimulant composition according to any one of items 1 to 7 above to the flavor and fragrance composition, beverage or food product, fragrance or cosmetic product, daily utensil product, oral composition, or pharmaceutical product.

11. Vanillin acetals represented by the general formula (1'):

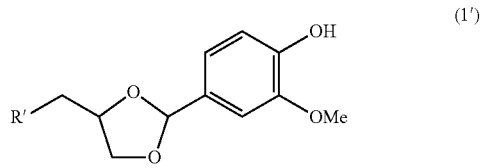

wherein R' represents a straight chain or branched alkyl group having 4 to 9 carbon atoms, or a straight chain or branched alkoxy group having 1 to 8 carbon atoms.

12. A kit comprising a sports rub gel or cream, said sports rub gel or cream comprising a composition of any one of the preceding items 1 to 10.

13. A kit comprising a shaving gel or cream, said shaving gel or cream comprising a composition of any one of items 1 to 10.

14. A kit comprising a personal care product, said personal care product comprising a composition of any one of items 1 to 10.

15. A method of relieving sore muscles comprising topically applying a composition of any one of items 1 to 10.

16. A method of preparing a topical medicine or topical analgesic lotion cream or spray comprising adding the composition of any one of items 1 to 10 to a biologically active agent.

17. A method of increasing the effect of one or more sensate materials contained in a composition comprising adding an effective amount of vanillin acetals represented by the general formula (1):

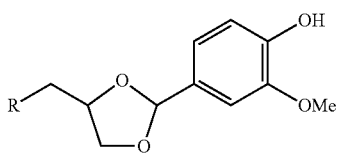

(1)

wherein R represents a hydrogen atom, a straight chain or branched alkyl group having 1 to 9 carbon atoms, or a straight chain or branched alkoxy group having 1 to 8 carbon atoms
to the composition containing the sensate materials.

18. The composition of any one of items 1 to 10, wherein the composition is in a form suitable for topical delivery.

Advantageous Effect of the Invention

The vanillin acetals of the invention can be easily synthesized, have the strong pungent and/or warming sensation effect with an excellent long-lasting effect thereof, and are useful as sensory stimulants. In the case where the vanillin acetals are added to a cooling sensation agent, they impart the cooling sensation-emphasizing effect. They also impart the pungent and/or warming sensation effect and cooling sensation-emphasizing effect having an excellent lasting effect thereof to various kinds of beverage or food products, oral compositions, and fragrance or cosmetic products when they are added to the product. Further, they have an excellent property that they scarcely cause undesirable skin stimulating feeling to the human body. In addition, they are not colored during storage, thus being excellent in stability.

DETAILED DESCRIPTION OF THE PREFERRED EMBODIMENT

Hereinafter, the invention will be described more in detail.

A sensory stimulant composition of the invention contains vanillin acetals represented by the above-mentioned general formula (1), and functions as, for example, a pungent agent composition, a warming sensation agent composition, and a cooling sensation agent composition depending on the constitution thereof. The vanillin acetals represented by the general formula (1) of the invention are compounds having a strong pungent and/or warming sensation effect together with an excellent long-lasting effect thereof, and also having an excellent cooling sensation-emphasizing effect. If the compound can impart sensory stimulation such as a pungent and/or warming sensation effect and a cooling sensation-emphasizing effect to various kinds of products even when compound is used alone, the compound itself is also included in the notion of the sensory stimulant composition of the invention.

With respect to the sensory stimulant compound represented by the above-mentioned general formula (1) to be contained in the sensory stimulant composition of the invention, the group R represents a hydrogen atom, a straight chain or branched alkyl group having 1 to 9 carbon atoms, or a straight chain or branched alkoxy group having 1 to 8 carbon atoms. Specific examples of the straight chain or branched alkyl group having 1 to 9 carbon atoms for R in the general formula (1) include methyl, ethyl, n-propyl, isopropyl, n-butyl, isobutyl, sec-butyl, tert-butyl, pentyl, hexyl, heptyl, octyl, and nonyl groups. Specific examples of the straight chain or branched alkoxy group having 1 to 8 carbon atoms include methoxy, ethoxy, n-propoxy, isopropoxy, n-butoxy, isobutoxy, sec-butoxy, tert-butoxy, pentyloxy, hexyloxy, heptyloxy, and octyloxy groups.

Specific examples of the vanillin acetals represented by the general formula (1) of the invention include, for example, vanillin-1,2-propylene glycol acetal, vanillin-1,2-butylene glycol acetal, vanillin-1,2-pentylene glycol acetal, vanillin-1,2-hexylene glycol acetal, vanillin-1,2-heptylene glycol acetal, vanillin-1,2-octylene glycol acetal, vanillin-1,2-nonylene glycol acetal, vanillin-1,2-decylene glycol acetal, vanillin-1,2-undecylene glycol acetal, vanillin-1-methoxyglycerol acetal, vanillin-1-ethoxyglycerol acetal, vanillin-1-propoxyglycerol acetal, vanillin-1-butoxyglycerolacetal, vanillin-1-pentoxyglycerol acetal, vanillin-1-hexyloxyglycerol acetal, vanillin-1-(2-ethyl)hexyloxyglycerol acetal, vanillin-1-heptyloxyglycerol acetal, and vanillin-1-octyloxyglycerol acetal. Preferable examples among the vanillin acetals represented by the general formula (1) are vanillin-1,2-butylene glycol acetal, vanillin-1,2-hexylene glycol acetal, vanillin-1-methoxyglycerol acetal, vanillin-1-butoxyglycerol acetal, and vanillin-1-(2-ethyl)hexyloxyglycerol acetal.

On the other hand, vanillin acetals represented by a general formula (1') of the invention which are vanillin acetals represented by the general formula (1) excluding the case where R is a hydrogen atom or an alkyl group having 1 to 3 carbon atoms are conventionally unknown novel compounds. Examples of the straight chain or branched alkyl group having 4 to 9 carbon atoms and straight chain or branched alkoxy group having 1 to 8 carbon atoms for R' in the general formula (1') as well as examples of vanillin acetals are respectively the same as those exemplified for the general formula (1). Since the carbon atom at the fourth position of the 1,3-dioxolan ring in the general formula (1) is an asymmetric carbon atom, the vanillin acetals represented by the general formula (1) can form optically active isomers and racemic modifications. In the invention, the vanillin acetals represented by the general formula (1) may be optically active isomers or racemic modifications and also include these optically active isomers or racemic modifications.

The vanillin acetals represented by the general formula (1) including the general formula (1') are synthesized, for example, in accordance with the following reaction formula:

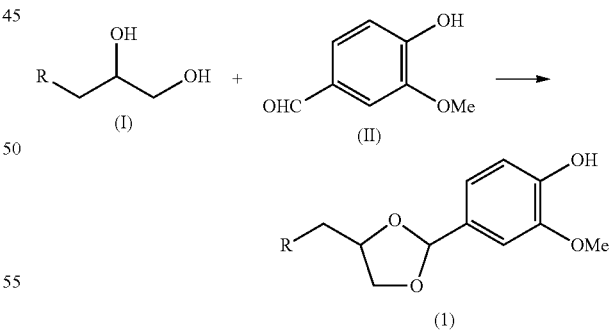

wherein R have the same meanings as defined above.

That is, compounds represented by the general formula (1) are easily produced by reacting glycols represented by the general formula (I) and vanillin represented by the formula (II) in the presence of an acidic substance, followed by dehydrating and condensing the product obtained.

The acidic substance to be used in the above-mentioned synthesis includes various kinds of acidic substances such as Brønsted acids and Lewis acids, and specific examples thereof include sulfonic acids such as benzenesulfonic acid, p-toluenesulfonic acid, methanesulfonic acid, camphorsulfonic acid, and sulfuric acid; perhalogenoacetic acids such as trifluoroacetic acid and trichloroacetic acid; and Lewis acids such as ferric chloride, zinc chloride, and stannic chloride. Preferable examples of the acidic substance include p-toluenesulfonic acid, methanesulfonic acid, and camphorsulfonic acid. Among these, p-toluenesulfonic acid and methanesulfonic acid are more preferable as they have versatility and high reaction selectivity and give objective substance in high yield. These acidic substances may be used alone or in combination of two or more thereof, and it is preferable to be used alone.

The reaction can be carried out in an organic solvent. Examples of the organic solvent include aromatic hydrocarbons such as toluene, benzene, chlorobenzene, and xylene; aliphatic hydrocarbons such as hexane, heptane, and octane; alicyclic hydrocarbons such as cyclohexane, methylcyclohexane, and decalin; ethers such as diethyl ether, diisopropyl ether, and tetrahydrofuran; halo hydrocarbons such as dichloromethane and dichloroethane; and so on. They may be use alone or in combination of two or more thereof. Preferable solvents are aromatic hydrocarbons and among these toluene and xylene are more preferable since they have versatility and high reaction selectivity and give objective substances in high yield.

The amount of solvent to be used is not particularly limited and is usually in a range of about 0.1 to 10 times by volume as much as that of raw material compounds (reactants) and preferably in a range of about 0.5 to 3 times by volume as much as that of the raw material compounds (substrate). The amount of the acidic substance to be used in the reaction is preferably 0.1 to 10% by weight and more preferably 0.5 to 5% by weight to 1 part by weight of the raw material compounds (substrate), but the range is not limited to the range described above. The reaction temperature is usually about 50° C. to about 200° C., and preferably around the boiling point of the solvent to be used. The reaction can be smoothly carried out when the reaction is conducted by keeping the above mentioned temperature for about 1 hour to about 50 hours, preferably 1 to 10 hours. After the completion of the reaction, the solvent is removed out under reduced pressure from the reaction solution obtained by the above-mentioned reaction. The obtained residue is distilled under reduced pressure to produce the vanillin acetals of the invention.

The vanillin acetals represented by the general formula (1) of the invention, which is obtained by the above-mentioned method, have a strong and lasting pungent and/or warming sensation effect, and they can be used as sensory stimulants alone and as they are.

The application range and application method of the vanillin acetals to be obtained in the invention should be properly changed depending on the type of the products used or purpose of using the products. The amount of vanillin acetals used is usually in a range of 0.0001 to 90% by weight for a flavor and fragrance composition, and is about $1\times10^{-7}$% by weight or higher, usually 0.0001 to 20% by weight and preferably 0.001 to 5% by weight to the total compositions of products in the case of addition to a beverage or food product, a fragrance or cosmetic product, a daily utensil product, an oral composition, or a pharmaceutical product.

Further, the sensory stimulant composition of the invention is used in combination with one or more kinds of components selected from cooling sensation substances to produce a sensory stimulant composition with heightened cooling sensation intensity.

Examples of the cooling sensation substances include menthol, menthone, camphor, pulegol, isopulegol, cineole, mint oil, peppermint oil, spearmint oil, eucalyptus oil, 3-l-menthoxypropane-1,2-diol, N-alkyl-p-menthane-3-carboxamide, 3-l-menthoxy-2-methylpropane-1,2-diol, p-menthane-3,8-diol, 2-l-menthoxyethan-1-ol, 3-l-menthoxypropan-1-ol, 4-l-menthoxybutan-1-ol, menthyl 3-hydroxybutanate, menthyl lactate, menthone glycerin ketal, 2-(2-l-menthyloxyethyl)ethanol, menthyl glyoxylate, 1-(2-hydroxy-4-methylcyclohexyl)ethanone, N-methyl-2,2-isopropylmethyl-3-methylbutanamide, menthyl 2-pyrrolidone-5-carboxylate, monomenthyl succinate, alkali metal salts of monomenthyl succinate, alkaline earth metal salts of monomenthyl succinate, monomenthyl glutarate, alkali metal salts of monomenthyl glutarate, alkali earth metal salts of monomenthyl glutarate, N-[[5-methyl-2-(1-methylethyl)-cyclohexyl]carbonyl] glycine, p-menthane-3-carboxylic acid glycerol ester, Menthol propylene glycol carbonate; Menthol ethylene glycol carbonate, and 6-isopropyl-3,9-dimethyl-1,4-dioxaspiro [4.5]decan-2-one. Other cooling senates are disclosed in U.S. Pat. Nos. 7,030,273 and 6,780,443, which are hereby incorporated by reference in their entirety. One or two of these compounds may be used by compounding properly.

The vanillin acetals of the invention and the cooling sensation substances not included in the vanillin acetals of the invention are mixed and used at any optional ratio within a range wherein the effects of the invention are not spoiled. The ratio by weight of the vanillin acetals and the cooling sensation substances not included therein is preferably within a range of (1:99) to (70:30). In the case of imparting a cooling sensation effect, the mixing ratio of the vanillin acetals of the invention and cooling sensation substances may be within a range in which the pungent and/or warming sensation effect due to the addition of the vanillin acetals does not arise, and the amount of the vanillin acetals to the cooling sensation substance is usually 0.001 to 0.95 times, preferably 0.01 to 0.5 times as much as the total amount of the cooling sensation substances. When the sensory stimulant compositions of the invention is prepared by adding the vanillin acetals to the cooling sensation substance at the above-mentioned ratio, the cooling sensation effect are further improved and increased.

In the case of imparting a pungent and/or warming sensation effect, the amount of the sensory stimulant composition added may be within a range in which no cooling sensation effect due to addition of cooling sensation substances is caused, and it is generally 0.001 to 0.95 times, preferably 0.01 to 0.5 times as much as the total amount of the vanillin acetals.

The sensory stimulant compositions of the invention may further contain other sensory stimulants not included in the vanillin acetals represented by the general formula (1) in combination.

Examples of other sensory stimulants include vanillyl ethyl ether, vanillyl propyl ether, capsaicine, gingerol, vanillyl butyl ether, acetic acid ester of vanillyl butyl ether, 4-(l-menthoxymethyl)-2-phenyl-1,3-dioxolan, 4-(l-menthoxymethyl)-2-(3',4'-dihydroxyphenyl)-1,3-dioxolan, 4-(l-menthoxymethyl)-2-(2'-hydroxy-3'-methoxyphenyl)-1,3-dioxolan, 4-(l-menthoxymethyl)-2-(4'-methoxyphenyl)-1,3-dioxolan, 4-(l-menthoxymethyl)-2-(3',4'-methylenedioxyphenyl)-1,3-dioxolan, 4-(l-methoxymethyl)-2-(3'-methoxy-4'-hydroxyphenyl)-1,3-dioxolan, redpepper oil, redpepper oleoresin, ginger oleoresin, nonylic acid vanillyl amide, jamboo oleoresin, *Zanthoxylum piperitum* extract, sanshool I, sanshool II, sanshoamide, black pepper extract, chavicine, piperine, and spilanthol. These compounds may be properly used alone or in combination of two or more thereof.

The mixing ratio of the vanillin acetals of the invention and other sensory stimulants not included in the vanillin acetals of the invention may be within a range in which no warming sensation effect is imparted by the addition of the warming sensation substance when the object of adding the sensory stimulant composition is to impart a cooling sensation effect. The amount of the warming sensation substance added is generally 0.001 to 0.95 times, preferably 0.01 to 0.5 times as much as the total amount of the cooling sensation agent composition.

In the invention, the above-mentioned sensory stimulant composition may be at first added to a flavor and fragrance composition to obtain a sensory stimulant composition-containing flavor and fragrance composition (a flavor and fragrance composition of the invention), and then the sensory stimulant composition-containing flavor and fragrance composition obtained may be added to the product. In another case, vanillin acetals, other sensory stimulants and cooling sensation substances may be added separately and directly to the flavor and fragrance composition.

Examples of the other flavor and fragrance components to be contained together with the sensory stimulant composition of the invention include various kinds of synthetic aroma chemicals, natural essential oils, natural aroma chemicals, citrus oils, and animal aroma chemicals. As such flavor and fragrance components, a wide variety of flavor and fragrance components described in, for example, Collection of Known and Customary Technologies (SHU-CHI/KANYOH GIJUTSU SHU)—Flavor and Fragrance Materials—, Part I, Jan. 29, 1999, JPO can be used. Specific examples of the components include α-pinene, limonene, cis-3-hexenol, phenyl ethylalcohol, styraryl acetate, eugenol, methyl dihydrojasmonate, rose oxide, linarol, benzaldehyde, muscone, Musk T (manufactured by TAKASAGO INTERNATIONAL CORPORATION), and THESARON (manufactured by TAKASAGO INTERNATIONAL CORPORATION).

The content of the sensory stimulant composition in the sensory stimulant composition-containing flavor and fragrance composition of the invention can be properly adjusted in accordance with the types of the flavor or fragrance and other components to be added and the purpose of using the sensory stimulant composition-containing flavor and fragrance composition. For example, in the case of a fragrance composition, the content of the sensory stimulant composition is, in general, preferably 0.001 to 50% by weight, particularly preferably 0.01 to 20% by weight to the total weight of the fragrance composition. In the case of a flavor composition, the content of the sensory stimulant composition is, in general, preferably 0.0001 to 50% by weight, particularly preferably 0.01 to 30% by weight to the total weight of the flavor composition.

The sensory stimulant composition-containing flavor and fragrance composition of the invention containing the sensory stimulant composition may contain one or more kinds of flavor and fragrance retention agents commonly employed in flavor and fragrance compositions, if necessary. Examples of other flavor and fragrance retention agents to be used include ethylene glycol, propylene glycol, dipropylene glycol, glycerin, hexylene glycol, benzyl benzoate, triethyl citrate, diethyl phthalate, hercolyn, middle chain fatty acid triglyceride, and middle chain fatty acid diglyceride, and one or more kinds of these compounds may be added.

As described above, the sensory stimulant composition of the invention may be use alone or in form of the sensory stimulant composition-containing flavor and fragrance composition containing the sensory stimulant composition in order to impart the sensory stimulation to various kinds of products. As the products to which the sensor stimulation can be imparted by adding the sensory stimulant composition itself or the sensory stimulant composition-containing flavor and fragrance composition containing the sensory stimulant composition, there exemplified beverage or food products, fragrance or cosmetic products, daily utensil products, oral compositions, and pharmaceutical products.

The products to which the sensor stimulation can be imparted by adding the sensory stimulant composition or the sensory stimulant composition-containing flavor and fragrance composition containing the sensory stimulant composition will be described more in detail below. First, specific examples of the beverage or food products include beverages such as fruit juice beverages, fruit liquors, milk drinks, carbonated beverages, refreshing drinks, and health and nutrient drinks; frozen confectionery such as ice creams, sherbets, and Popsicle; desserts such as jelly and pudding; confections such as cakes, cookies, chocolates, and chewing gum; Japanese sweets such as bean-jam buns (Manju), thick jellied sweet made of azuki bean paste (Yokan) and thick jellied sweet made of powdered rice paste (Uiro); jams; candies; breads; tea drinks and other favorite drinks such as green tea, oolong tea, black tea, persimmon leaf tea, chamomile tea, sasa veitchii tea, mulberry leaf tea, *Houttuynia cordata* tea, puaar tea, mate tea, rooibos tea, gymnema tea, guava tea, coffee and cocoa; soups such as Japanese style soups, Western style soups and Chinese style soups; flavor seasonings; various kinds of instant beverages or food products; various kinds of snack foods; and compositions for oral use. However the examples of the beverage or food products are not particularly limited to the above-mentioned products.

Examples of the fragrance or cosmetic products or daily utensil products to which the fragrance can be imparted by adding the sensory stimulant composition or the sensory stimulant composition-containing flavor and fragrance composition of the invention include flavor and fragrance products, skin-care cosmetics, make-up cosmetics, hair cosmetics, anti-sunburn cosmetics, medicinal cosmetics, hair-care products, soaps, body lotions, agents for bathing, detergents, soft finishing agents, cleaning agents, kitchen detergents, bleaching agents, aerosol agents, deodorant-aromatics, repellents, tobacco, and other groceries.

Examples of the fragrance or cosmetic products and daily utensil products are shown more specifically below.

Examples of the fragrance products include perfume, Eau de Perfum, Eau de Toilette, and Eau de Cologne.

Examples of the skin-care cosmetics include face washing creams, varnishing creams, cleansing creams, cold creams, massage creams, milky lotions, skin lotions, beauty wash, packs, and make-up removers.

Examples of the make-up cosmetics include foundations, face powders, pressed powders, talcum powders, rouge, lipsticks, lip creams, cheek rouge, eyeliners, mascara, eye shadows, eyebrow-color, eye packs, nail enamels, and enamel removers.

Examples of the hair cosmetics include pomades, brilliantine, setting lotions, hair sticks, hair solids, hair oils, hair treatments, hair creams, hair tonics, hair liquids, hair sprays, bandlin, hair-growing lotion, and hair dyes.

Examples of the anti-sunburn cosmetics include suntan products and sun screen products.

Examples of the medicinal cosmetics include antiperspirants, after-shaving lotions and gels, permanent wave agent, medicinal soaps, medicinal shampoos, and medicinal skin care cosmetics.

Examples of the hair-care products include shampoos, rinses, rinse-in-shampoo, hair conditioners, hair treatments, and hair packs.

Examples of the soaps include toilet soaps, bath soaps, perfume soaps, clear soaps, and synthetic soaps.

Examples of the body lotions include body soaps, body shampoos, and hand soaps.

Examples of the agents for bathing include bathing agents (e.g., bath salts, bath tablets, bath liquids, and the like), foam bath (bubble bath and the like), bath oils (e.g. bath perfumes, bath capsules and the like), milk bath, bath jelly, and bath cubes.

Examples of the detergents include heavy detergents for clothes, light detergents for clothes, liquid laundry detergents, laundry soaps, compact detergents, and powder soaps.

Examples of the soft finishing agents include softeners and furniture cares.

Examples of the cleaning agents include cleansers, house washes, toilet cleaners, bath cleaners, glass cleaners, fungicide, and cleaners for drain pipes.

Examples of the kitchen detergents include kitchen soaps, kitchen synthetic soaps, and dish washes.

Examples of the bleaching agents include oxidant bleaches (chlorine bleaches, oxygen bleaches, and the like), reductive bleaches (sulfur containing bleaches and the like), and optical bleaches.

Examples of the aerosol agents include spray type aerosols or powder spray.

Examples of the deodorant-aromatics include solid type, gel type or liquid type deodorizers and aromatics.

Examples of groceries include tissue paper and toilet paper.

Examples of the compositions for oral care include toothpastes, mouth cleaners, mouth wash, troches, and chewing gums.

Examples of the medical products include external use medicines such as poultices and ointments, and internal medicines.

In the case where the sensory stimulant composition and the sensory stimulant composition-containing flavor and fragrance composition of the invention are used for imparting the sensory stimulation to the various types of the above-exemplified products, the sensory stimulant composition or the sensory stimulant composition-containing flavor and fragrance composition may be added directly to the products depending on the types of the product or final states (product states, e.g. liquid phase, solid phase, powder phase, gel state, mist state, aerosol state, or the like) of the products; or may be added or supplied as a form of liquid dissolved in alcohols or polyhydric alcohols such as propylene glycol and glycerin; or may be added or supplied as a form solubilized, emulsified or dispersed by using natural gums such as gum arabic and tragacanth gum or surfactants (e.g. nonionic surfactants such as fatty acid esters of glycerin and fatty acid esters of sucrose, anionic surfactants, cationic surfactants, and amphoteric surfactants); or may be added or supplied as powders formed by coating with excipient, e.g. natural gums such as gum arabic, gelatin, and dextrin; or may be added or supplied as microcapsules encapsulated by treating with encapsulating agents.

Further, the sensory stimulant composition and the sensory stimulant composition-containing flavor and fragrance composition may be added to the product as a form enclosed in an enclosing agent such as cyclodextrin to be stabilized and sustained release.

In the case of imparting the sensory stimulation to the product, the amount of the sensory stimulant composition added or supplied to products may be properly to the types and states of the products and the sensory stimulating effect or action demanded for the product. Generally, the amount of the sensory stimulant composition added or supplied to products is preferably about $1\times10^{-7}$ to 0.1% by weight and more preferably $1\times10^{-6}$ to 0.01% by weight to the weight of the products.

EXAMPLES

Hereinafter, the invention will be described in more detail with reference to examples that, however, do not limit by any way. The examples may be modified within a scope not deviated from the scope of the invention.

The apparatuses employed for determining physical properties of the products in the examples are as follows:

(1) Proton Nuclear Magnetic Resonance Spectrum ($^1$H-NMR);

Device: NMR spectrometer "DRX-500" (500 MHz), manufactured by Bruker Japan Co., Ltd.

Internal standard substance: tetramethylsilane (2) Infrared Absorption Spectrum (IR);

Device: Infrared absorption spectrometer "AVATER 360FT-IR" manufactured by Nicolet Inc.

Measurement method: film method (3) Mass Spectrum (MS);

Device: Mass spectrometer "M-80B" (ionization voltage: 20 eV), manufactured by Hitachi Ltd.

(4) Gas Chromatogram (Measurement of Conversion Ratio);

Device: Gas chromatograph mass spectrometer "HP-5890 A" manufactured by Hewlett-Packard Company Column: HP-5 (30 m×0.32 mm×0.25 μm), manufactured by Hewlett-Packard Company Example 1

Synthesis of vanillin-1,2-hexylene glycol acetal (compound A)

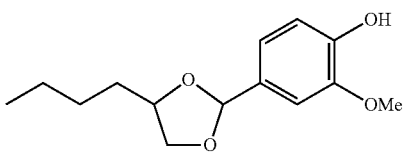

(Compound A)

Into a 300 ml reaction flask with a thermometer, a Dean-Stalk tube and a refluxing tube, 25.0 g of vanillin (molecular weight 152.14, 164.31 mmol), 21.36 g of hexylene glycol (molecular weight 118.18, 180.74 mmol), 150 mg of p-toluenesulfonic acid monohydrate (molecular weight 190.22, 789 μmol), and 150 ml of toluene were charged, and the mixture was heated and refluxed in an oil bath at 140° C. under nitrogen current. While removing formed water through the Dean-Stalk tube, the mixture was continuously refluxed. After heated for 4.5 hours, disappearance of raw materials was confirmed by the gas chromatogram. The reaction solution obtained was quenched in an aqueous sodium carbonate solution, extracted with toluene, washed with salt water, and dried with dehydrated sodium sulfate. After filtration, the solvent in the extract solution was removed by a rotary evaporator and then subjected to vacuum distillation to obtain an aimed compound, vanillin-1,2-hexylene glycol acetal (molecular weight 252.31), in form of a colorless transparent oil. The production amount was 39.73 g (157.47 mmol); the purity was 100% (isomer ratio 54.3:43.7); the yield was 95.8%; and the boiling point was 127 to 129° C. (9 to 15 Pa).

$^1$H-NMR (500 MHz, CDCl$_3$, δ) ppm: 0.90-0.94 (m, 3H), 1.32-1.42 (m, 2H), 1.52-1.62 (m, 2H), 3.46-3.57 (m, 2H), 3.51-3.66 (m, 2H), 3.80-3.99 (m, 1H), 4.07-4.28 (m, 1H), 4.33-4.45 (m, 1H), 3.80-3.99 (m, 1H), 5.76-5.86 (m, 2H), 6.88-6.92 (m, 1H), 6.96-7.02 (m, 2H).

IR cm$^{-1}$: 3501, 3077, 2961, 2873, 1657, 1472, 1455, 1414, 1369, 1259, 1171, 1093, 1032, 992, 899.

MS (m/e): 200 (M$^-$), 183, 167, 157, 145, 128, 110, 95, 85, 83, 73, 55, 43, 29.

Example 2

Synthesis of vanillin-1,2-butylene glycol acetal (compound B)

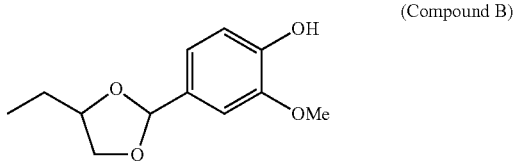 [SMILES: CCC1COC(c2ccc(O)c(OC)c2)O1]

(Compound B)

Into a 300 ml reaction flask with a thermometer, a Dean-Stalk tube and a refluxing tube, 30.0 g of vanillin (molecular weight 152.15, 197.17 mmol), 19.55 g of 1,2-butylene glycol (molecular weight 90.12, 216.89 mmol), 150 mg of p-toluenesulfonic acid monohydrate (molecular weight 190.22, 789 μmol), and 150 ml of toluene were charged, and the mixture was heated and refluxed in an oil bath at 135° C. under nitrogen current. While removing formed water through the Dean-Stalk tube, the mixture was continuously refluxed. After heated for 4 hours, disappearance of raw materials was confirmed by the gas chromatogram. The reaction solution obtained was quenched in an aqueous sodium carbonate solution, extracted with toluene, washed with salt water, and dried with dehydrated sodium sulfate. After filtration, the solvent in the extract solution was removed by rotary evaporator and subjected to vacuum distillation to obtain an aimed compound, vanillin-1,2-butylene glycol acetal in form of a colorless transparent oil. The production amount was 41.70 g (molecular weight 224.26, 185.93 mmol); the purity was 100% (isomer ratio 53.7:46.3); the yield was 94.3%; and the boiling point was 127 to 129° C. (30 to 32 Pa).

$^1$H-NMR (500 MHz, CDCl$_3$, δ) ppm: 0.99-1.05 (m, 3H), 1.56-1.83 (m, 2H), 3.63 (t, J=7.1 Hz, 0.4H), 3.71 (t, J=7.1 Hz, 0.6H), 3.92 (s, 3H), 4.09 (t, J=7.1 Hz, 0.6H), 4.12-4.21 (m, 1H), 4.24-4.30 (m, 0.4H), 5.67-5.69 (m, 1H), 5.75 (s, 0.6H), 5.84 (s, 0.4H), 6.89-6.93 (m, 1H), 6.97-7.03 (m, 2H).

IR (membrane) cm$^{-1}$: 3412, 2966, 2879, 1611, 1519, 1464, 1436, 1405, 1370, 1277, 1241, 1165, 1078, 1032, 956, 860, 823, 779.

MS (m/e): 224 (M$^+$), 207, 195, 169, 165, 151, 137, 124, 101, 93, 81, 65, 55, 39.

Example 3

Synthesis of vanillin-1-butoxyglycerol acetal (compound C)

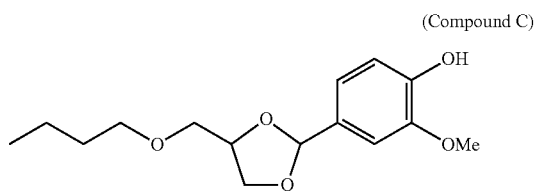 [SMILES: CCCCOCC1COC(c2ccc(O)c(OC)c2)O1]

(Compound C)

Into a 300 ml reaction flask with a thermometer, a Dean-Stalk tube and a refluxing tube, 25.0 g of vanillin, (molecular weight 152.14, 164.31 mmol), 24.35 g of 1-butoxyglycerol (molecular weight 148.20, 164.31 mmol), 150 mg of p-toluenesulfonic acid monohydrate (molecular weight 190.22, 789 μmol), and 150 ml of toluene were charged, and the mixture was heated and refluxed in an oil bath at 140° C. under nitrogen current. While removing formed water through the Dean-Stalk tube, the mixture was continuously refluxed. After heated for 5 hours, disappearance of raw materials was confirmed by gas chromatogram. The reaction solution obtained was quenched in an aqueous sodium carbonate solution, extracted with toluene, washed with salt water, and dried with dehydrated sodium sulfate. After filtration, the solvent in the extract solution was removed by a rotary evaporator and subjected to vacuum distillation to obtain an aimed compound, vanillin-1-butoxyglycerol acetal in form of a colorless transparent oil. The production amount was 43.76 g (molecular weight 282.34, 155.99 mmol); the purity was 100% (isomer ratio 54.3:43.7); the yield was 94.3%; and the boiling point was 143 to 152° C. (4.0 Pa).

$^1$H-NMR (500 MHz, CDCl$_3$, δ) ppm: 0.90-0.94 (m, 3H), 1.32-1.42 (m, 2H), 1.52-1.62 (m, 2H), 3.46-3.57 (m, 3H), 3.60-3.66 (m, 1H), 3.83 (t, J=7.0 Hz, 0.4H), 3.90 (s, 3H), 3.95 (t, J=7.0 Hz, 0.6H), 4.08 (t, J=7.0 Hz, 0.6H), 4.25 (t, J=7.0 Hz, 0.4H), 4.33-4.43 (m, 1H), 5.67-5.70 (m, 1H), 5.74 (s, 0.6H), 5.85 (s, 0.4H), 6.88-6.92 (m, 1H), 6.96-7.02 (m, 2H).

IR (membrane) cm$^{-1}$: 3416, 2957, 2870, 1611, 1519, 1464, 1374, 1277, 1241, 1164, 1118, 1034, 969, 860, 822, 778, 717

MS (m/e): 282 (M$^+$), 195, 168, 159, 151, 137, 124, 109, 93, 81, 57, 41.

Example 4

Synthesis of vanillin-1-(2-ethyl)hexyloxyglycerol acetal (compound D)

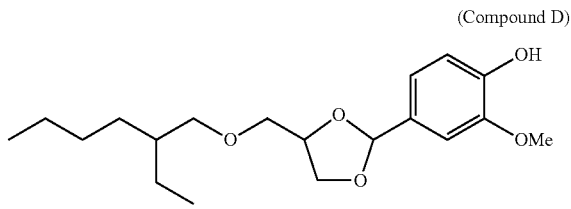 [SMILES: CCCCC(CC)COCC1COC(c2ccc(O)c(OC)c2)O1]

(Compound D)

Into a 300 ml reaction flask with a thermometer, a Dean-Stalk tube and a refluxing tube, 20.0 g of vanillin (molecular weight 152.14, 131.46 mmol), 26.86 g of 1-(2-ethyl)hexyloxyglycerol (molecular weight 204.31, 131.46 mmol), 150 mg of p-toluenesulfonic acid monohydrate (molecular weight 190.22, 789 µmol), and 150 ml of toluene were charged, and the mixture was heated and refluxed in an oil bath at 140° C. under nitrogen current. While removing formed water through the Dean-Stalk tube, the mixture was continuously refluxed. After heated for 5 hours, disappearance of raw materials was confirmed by gas chromatogram. The reaction solution obtained was quenched in an aqueous sodium carbonate solution, extracted with toluene, washed with salt water, and dried with dehydrated sodium sulfate. After filtration, the solvent in the extract solution was removed by a rotary evaporator and subjected to vacuum distillation to obtain an aimed compound, vanillin-1-(2-ethyl)hexyloxyglycerol acetal in form of a colorless transparent oil. The production amount was 40.89 g (molecular weight 338.45, 120.81 mmol); the purity was 100% (isomer ratio 53.2:44.1); the yield was 91.9%; and the boiling point was 163 to 167° C. (10 to 14 Pa).

$^1$H-NMR (500 MHz, CDCl$_3$, δ) ppm: 0.82-0.95 (m, 6H), 1.20-1.48 (m, 10H), 3.30-3.42 (m, 2H), 3.46-3.52 (m, 0.5H), 3.52-3.57 (m, 0.5H), 3.86 (t, J=6.8 Hz, 0.5H), 3.90 (s, 3H), 3.94-4.00 (m, 0.5H), 4.25 (t, J=7.0 Hz, 0.5H), 4.32-4.43 (m, 1H), 5.64-5.67 (m, 1H), 5.74 (s, 0.5H), 5.84 (s, 0.5H), 6.87-6.92 (m, 1H), 6.95-7.02 (m, 2H).

IR (membrane) cm$^{-1}$: 3420, 2929, 1611, 1519, 1464, 1376, 1276, 1241, 1164, 1104, 1035, 969, 860, 820, 778.

MS (m/e): 338 (M$^+$), 321, 307, 239, 225, 215, 195, 168, 151, 137, 124, 103, 93, 71, 57, 43, 41.

Example 5

Sensory Evaluation 1

Compound A and Compound C obtained in Example 1 and Example 3, respectively, were subjected to oral evaluation using 10 ppm aqueous solutions of them by ten expert panelists having 5 or more year experience, and an instantaneous sensation and an intensity of warming sensation and pungent taste were evaluated on the basis of the following evaluation criteria. On the sensory evaluation, 4-(1-methoxymethyl)-2-(3'-methoxy-4'-hydroxyphenyl)-1,3-dioxolan (Comparative compound A: the compound described in JP-A-8-225564) was used as a comparative compound. The results are shown in Table 1. The evaluation results in the table show the average value of ten panelists.

<Evaluation Criteria of Instantaneous Sensation>
◎: very fast
○: fast
Δ: is somewhat slow
x: slow <Evaluation Criteria of Intensity>
5: very strong
4: strong
3: weak
2: very weak
1: not able to feel

TABLE 1

| Test compounds | Compound A | Compound C | Comparative compound A |
|---|---|---|---|
| Instantaneous sensation | ◎ | ◎ | Δ |
| Intensity | 4.5 | 4.2 | 2.8 |

All of Compound A, Compound C and Comparative compound A were almost odorless and had a strong pungent and warming effect in the mouth. They also had a strong warm sensation and stimulating effect on the skin.

Synthesis Example

Synthesis of Compounds 1 to 12 and Compound 16 in Table 2-1 and Table 2-2

Acetals of Compounds 1 to 12 and Compound 16 shown in Table 2-1 and Table 2-2 were synthesized according to the following general acetal synthesis method.

(General Acetal Synthesis Method)

Into a reaction vessel, 150 mmol of aryl aldehydes, 200 mmol of diols, 150 mg of p-toluenesulfonic acid monohydrate, and 150 ml of toluene are charged, and the mixture is heated and refluxed in an oil bath at 140° C. under nitrogen current. While removing formed water through the Dean-Stalk tube, the mixture is continuously refluxed and heated for 5 hours. At this point, disappearance of raw materials can be nearly confirmed by gas chromatogram. The reaction solutions obtained are quenched in an aqueous sodium carbonate solution, extracted with toluene, washed with salt water, and dried with dehydrated sodium sulfate. After filtration, the solvent in the extract solution is removed by a rotary evaporator. The crude product obtained is vacuum distilled or recrystallized to obtain an aimed vanillin acetal compound.

Example 6

Sensory Evaluation 2

Compounds 1 to 17 including Compounds A to D shown in Tables 2-1 and 2-2 were evaluated for their pungent taste and warming sensation effect in the mouths in the same manner as in Example 5. The evaluation was carried out on the basis of the following 4-grade evaluation criteria. The results are shown in Table 2-1 and Table 2-2.

<Evaluation Criteria>
◎: very high
○: high
Δ: effective but slight
x: little or not TABLE 2-1
| | Synthetic compounds and Effects | | |
|---|---|---|---|
| | Compound | Form | Effect |
| 1 | 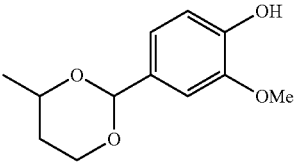 [SMILES: COc1cc(C2OCCC(C)O2)ccc1O] | Colorless needle-like crystal | X |
| 2 | 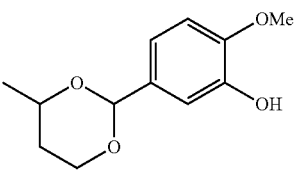 [SMILES: COc1ccc(C2OCCC(C)O2)cc1O] | Colorless needle-like crystal | X |
| 3 | 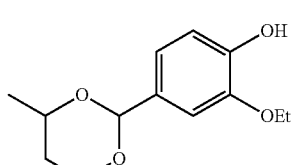 | Colorless needle-like crystal | X |
| 4 | 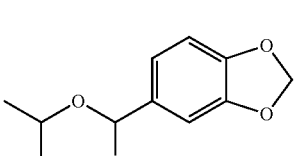 | Colorless needle-like crystal | X |
| 5 | 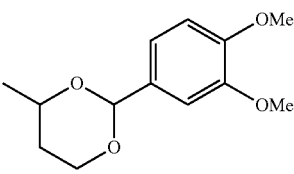 [SMILES: COc1ccc(C2OCCC(C)O2)cc1OC] | Pale yellow oil | X |
| 6 | 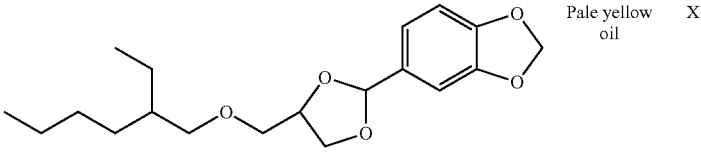 | Pale yellow oil | X |
| 7 | 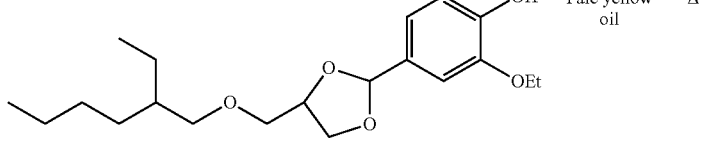 | Pale yellow oil | Δ |
| 8 | 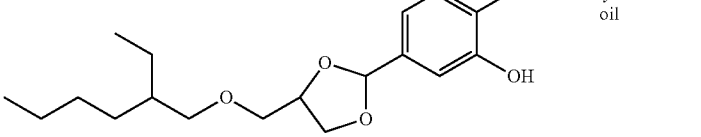 | Pale yellow oil | X |

TABLE 2-1-continued

Synthetic compounds and Effects

| Compound | | Form | Effect |
|---|---|---|---|
| 9 | [structure: 2-ethylhexyl ether-substituted dioxolane with 3,4-dimethoxyphenyl group] | Pale yellow oil | X |

TABLE 2-2

Synthetic compounds and Effects

| Compound | | Form | Effect |
|---|---|---|---|
| 10 | [structure: 1,3-dioxolane with 4-hydroxy-3-methoxyphenyl group] | Colorless oil | X |
| 11 | [structure: methyl-substituted dioxolane with 4-hydroxy-3-methoxyphenyl group] | Colorless oil | Δ |
| 12 | [structure: dimethyl-substituted dioxolane with 4-hydroxy-3-methoxyphenyl group] | Colorless oil | X |
| 13 | Compound B [structure: ethyl-substituted dioxolane with 4-hydroxy-3-methoxyphenyl group] | Colorless oil | ◎ |
| 14 | Compound A [structure: butyl-substituted dioxolane with 4-hydroxy-3-methoxyphenyl group] | Colorless oil | ◎ |
| 15 | Compound C [structure: butoxymethyl-substituted dioxolane with 4-hydroxy-3-methoxyphenyl group] | Colorless oil | ◎ |

TABLE 2-2-continued

Synthetic compounds and Effects

| | Compound | Form | Effect |
|---|---|---|---|
| 16 | [structure: dioxolane with MeO-CH2 group and 4-OH-3-OMe phenyl] | Colorless oil | ◎ |
| 17 | Compound D [structure: 2-ethylhexyloxymethyl dioxolane with 4-OH-3-OMe phenyl] | Pale yellow oil | ◎ |

As obvious from Table 2-1 and Table 2-2, the compounds of the invention (Compounds 11, 13 to 17) were found to have an excellent pungent taste and warming sensation effect as compared with the Comparative compounds (Compounds 1 to 10 and 12).

Example 7

Skin Cosmetic

The following ingredients were mixed by a homo-mixer, and then purified water was added thereto for adjusting the volume of the mixture to be 100 parts by weight to prepare a skin cosmetic. The skin cosmetic obtained was directly applied to the skins of ten common panelists of age 20 to 40 and then wiped out with a towel to evaluate its feeling after used. As a result, all the panelists replied as that the skin cosmetic of this example gave a warming sensation and showed a lasting warming sensation effect.

| <Prescription of Skin cosmetic> | |
|---|---|
| (Ingredients) | (Mixing amount) |
| Talc | 10.0 |
| Kaolin | 2.0 |
| Silicone powder | 10.0 |
| Compound A | 1.0 |
| Glycerin | 10.0 |
| Silicone oil | 8.0 |
| Vaseline | 2.0 |
| Squalan | 1.0 |
| Cholesteryl isostearate | 0.5 |
| Ceramide-2 | 0.1 |
| Hohoba oil | 1.0 |
| Ethanol | 10.0 |
| Floral fragrance | 0.5 |
| Ethylparaben | 0.3 |
| Purified water | balance |
| Total | 100.00 |

Example 8

Powdery Bath Agent

A powdery bath agent containing the following ingredients was prepared by a conventional method (the mixing amounts were based on part by weight). 30 g of the bath agent obtained was added in a bath water, and the feeling after bathing was evaluated by ten common panelists of age 20 to 40. As a result, all the ten panelists replied as that the agent gave a warming sensation and showed a continuous warming sensation effect.

| <Prescription of Powdery bath agent> | |
|---|---|
| (Ingredients) | (Mixing amount) |
| Compound B | 1.0 |
| Cetyl octanoate | 3.0 |
| Vanillyl butyl ether acetate | 0.5 |
| Hohoba oil | 2.0 |
| POE (6) stearyl ether | 1.2 |
| Cholesteryl hemisuccinate | 1.0 |
| POE (9) oleyl ether | 0.8 |
| Dextrin | 20.0 |
| Citrus fragrance | proper quantity |
| Colorant | proper quantity |
| Sodium hydrogencarbonate | 0.05 |
| Anhydrous sodium sulfate | balance |
| Total | 100.00 |

Example 9

Tablet Type Bath Agent

A tablet type bath agent containing the following ingredients was prepared by a conventional method (the mixing amounts were based on part by weight). 50 g of the bath agent obtained was added in a bath water, and the feeling after bathing was evaluated by ten common panelists of age 20 to 40. As a result, all the ten panelists replied as that the agent gave a warming sensation and showed a lasting warming sensation effect.

| <Prescription of tablet type bath agent> | |
|---|---|
| (Ingredients) | (Mixing amount) |
| Compound C | 1.0 |
| Cetyl octanoate | 3.0 |

-continued

| <Prescription of tablet type bath agent> | |
|---|---|
| (Ingredients) | (Mixing amount) |
| Hohoba oil | 2.0 |
| POE (6) stearyl ether | 1.2 |
| Cholesteryl hemisuccinate | 1.0 |
| Fumaric acid | 35.0 |
| POE (9) oleyl ether | 0.8 |
| Dextrin | 20.0 |
| Citrus fragrance | proper quantity |
| Colorant | proper quantity |
| Sodium carbonate | 18.0 |
| Sodium hydrogencarbonate | balance |
| Total | 100.00 |

Example 10

Chewing Gum

A chewing gum containing the following ingredients was prepared by a conventional method (the mixing amounts were based on part by weight). Each 3 g of the chewing gum obtained was chewed for 5 minutes by ten common panelists of age 20 to 40, and a warming sensation effect and a stimulus feeling of the gum were evaluated. As a result, all the ten panelists replied as that even after 1 hour the throat was still warm and a weakly stimulus feeling remained thereon.

| <Prescription of Chewing gum> | |
|---|---|
| (Ingredients) | (Mixing amount) |
| Compound A | 0.005 |
| 3-1-Menthoxy-1,2-propanediol | 0.005 |
| Gum base | 21.0 |
| Sugar powder | balance |
| Glutinous starch syrup | 11.4 |
| Citric acid | 0.8 |
| Mint flavor | 0.7 |
| Total | 100.00 |

Example 11

Mouth Wash

A mouth wash containing the following ingredients was prepared by a conventional method (the mixing amounts were based on part by weight). The mouth wash obtained was evaluated with respect to a warming sensation effect and a stimulus feeling by gargling after ten panelists kept 10 ml of the mouth wash in their mouths for 10 seconds. The panelists were common panelists of age 20 to 40. As a result, all the ten panelists replied as that even after 1 hour the throat was still warm and a weakly stimulating feeling remained thereon.

| <Prescription of mouth wash> | |
|---|---|
| (Ingredients) | (Mixing amount) |
| Compound B | 0.005 |
| 3-L-menthoxy-1,2-propanediol | 0.005 |
| Ethanol (95%) | 5.0 |

-continued

| <Prescription of mouth wash> | |
|---|---|
| (Ingredients) | (Mixing amount) |
| Polyoxyethylene hydrogenated caster oil (50 E.O.) | 2.0 |
| Glycerin | 10.0 |
| Sodium benzoate | 0.05 |
| Purified water | balance |
| Citrus flavor | 0.1 |
| Total | 100.0 |

Example 12

Clear Shampoo

A clear shampoo containing the following ingredients was prepared (the mixing amounts were based on part by weight). Ten common panelists of age 20 to 40 washed their hair by using each 5 g of the clear shampoo obtained, and a cooling sensation effect and a lasting effect of the cooling sensation thereof were evaluated. As a result, all the ten panelists replied as that the shampoo gave a cooling sensation and showed a lasting cooling sensation effect.

| <Prescription of transparent shampoo> | |
|---|---|
| (Ingredients) | (Mixing amount) |
| Polyquaternium 10 | 10.0 |
| Sodium laureth sulfate (aqueous 30% solution) | 300.0 |
| Lauroylsarcosine sodium salt (aqueous 30% solution) | 50.0 |
| Cocamide propene betaine | 100.0 |
| Cocamide diethanolamide | 40.0 |
| 1,3-Butylene glycol | 20.0 |
| Citric acid | 3.0 |
| Methylparaben | 2.0 |
| Propylparaben | 0.5 |
| Edetic acid disodium salt | 1.0 |
| L-menthol | 6.3 |
| 2-(2-L-menthyloxyethyl)ethanol | 0.6 |
| Compound D | 0.1 |
| Citrus fragrance | 3.0 |
| Purified water | balance |
| Total | 1000.0 |

Example 13

Toothpaste

A toothpaste containing the following ingredients was prepared (the mixing amounts were based on part by weight). Ten common panelists of age 20 to 40 brushed their teeth by using each 3 g of the toothpaste, and a cooling sensation effect and a lasting effect of a cooling sensation thereof were evaluated. As a result, all the ten panelists replied as that the toothpaste gave a cooling sensation and a lasting cooling sensation effect.

| <Prescription of toothpaste> | |
|---|---|
| (Ingredients) | (Mixing amount) |
| L-menthol | 0.25 |
| 2-(2-L-menthyloxyethyl)ethanol | 0.20 |
| Calcium hydrogenphosphate (dihydrate) | 50.00 |
| Glycerin | 25.00 |
| Sodium lauryl sulfate | 1.40 |
| Carboxymethyl cellulose sodium salt | 1.50 |
| Saccharin sodium salt | 0.20 |
| Sodium benzoate | 0.10 |
| Strawberry flavor (containing 20% by weight of compound A) (manufactured by TAKASAGO INTERNATIONAL CORPORATION) | 1.00 |
| Purified water | balance |
| Total | 100.00 |

Example 14

Flavor Composition for Tobacco

A flavor composition for tobacco containing the following ingredients was prepared (the mixing amounts were based on part by weight). When 0.1% of the obtained flavor composition for tobacco to which Compound D was added was applied to a tobacco on the market, the smoke from the tobacco exhibited mild feeling and a cool and refreshing feeling of menthol was emphasized by addition of the flavor composition.

| <Prescription of flavor composition for tobacco> | |
|---|---|
| (Ingredients) | (Mixing amount) |
| Menthol | 2.00 |
| Vanillin | 1.40 |
| Compound D | 0.10 |
| Heliotropine | 2.00 |
| Ethyl oxyhydrate | 0.80 |
| Ethyl butyrate | 0.25 |
| Ethyl valerianate | 0.25 |
| Linalool | 0.30 |
| Geraniol | 0.40 |
| Anethole | 1.60 |
| γ-Valerolactone | 0.80 |
| Cedarwood oil | 2.30 |
| Chamomile oil | 0.20 |
| Fennel oil | 0.20 |
| Furaneol | 1.00 |
| Ethyl alcohol | balance |
| Total | 100.00 |

The invention claimed is:

1. A sensory stimulant composition containing one or more of vanillin acetals represented by the general formula (1):

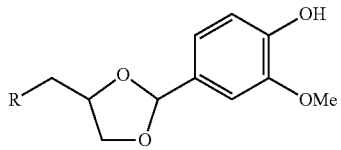

(1)

wherein R represents a straight chain or branched alkyl group having 1 to 9 carbon atoms, or a straight chain or branched alkoxy group having 1 to 8 carbon atoms.

2. The sensory stimulant composition according to claim 1, wherein the sensory stimulant composition is a pungent agent composition.

3. The sensory stimulant composition according to claim 1, wherein the sensory stimulant composition is a warming sensation agent composition.

4. The sensory stimulant composition according to claim 1, which further comprises one or more kinds of components selected from cooling sensation substances.

5. The sensory stimulant composition according to claim 4, wherein the cooling sensation substances are menthol, menthone, camphor, pulegol, isopulegol, cineole, mint oil, peppermint oil, spearmint oil, eucalyptus oil, 3-1-menthoxypropane-1,2-diol, N-alkyl-p-menthane-3-carboxamide, 3-1-menthoxy-2-methylpropane-1,2-diol, p-menthane-3,8-diol, 2-1-menthoxyethan-1-ol, 3-1-menthoxypropan-1-ol, 4-1-menthoxybutan-1-ol, menthyl 3-hydroxybutanate, menthyl lactate, menthone glycerin ketal, 2-(2-1-menthyloxyethyl) ethanol, menthyl glyoxylate, 1-(2 hydroxy-4-methylcyclohexyl)ethanone, N-methyl-2,2-isopropylmethyl-3-methylbutanamide, menthyl 2-pyrrolidone-5-carboxylate, monomenthyl succinate, alkali metal salts of monomenthyl succinate, alkaline earth metal salts of monomenthyl succinate, monomenthyl glutarate, alkali metal salts of monomenthyl glutarate, alkali earth metal salts of monomenthyl glutarate, N-([5-methyl-2-(1-methylethyl)-cyclohexyl]carbonyl] glycine, p-menthane-3-carboxylic acid glycerol ester, menthol propylene glycol carbonate, menthol ethylene glycol carbonate, and 6-isopropyl-3,9-dimethyl-1,4-dioxaspiro[4.5] decan-2-one.

6. The sensory stimulant composition according to any one of claims 1 to 5, further comprising one or more kinds of components selected from sensory stimulants consisting of a compound or compounds not included in the vanillin acetals represented by the general formula (1).

7. The sensory stimulant composition according to claim 6, wherein the sensory stimulants consisting of a compound or compounds not included in the vanillin acetals represented by the general formula (1) are one or more compounds selected from vanillyl ethyl ether, vanillyl propyl ether, capsaicin, gingerol, vanillyl butyl ether, vanillyl butyl ether acetate, 4-(1-menthoxymethyl)-2-phenyl-1,3-dioxolan, 4-(1-menthoxymethyl)-2-(3',4'-dihydroxyphenyl)-1,3-dioxolan, 4-(1-menthoxymethyl)-2-(2'-hydroxy-3'-methoxyphenyl)-1,3-dioxolan, 4-(1-menthoxymethyl)-2-(4'-methoxyphenyl)-1,3-dioxolan, 4-(1-menthoxymethyl)-2-(3',4'-methylenedioxyphenyl)-1,3-dioxolan, 4-(1-menthoxymethyl)-2-(3'-methoxy-4'-hydroxyphenyl)-1,3-dioxolan, red pepper oil, red pepper oleoresin, ginger oleoresin, nonylic acid vanillyl amide, jamboo oleoresin, Zanthoxylum piperitum extract, sanshool I, sanshool II, sanshoamide, black pepper extract, chavicine, pipeline, and spilanthole.

8. The sensory stimulant composition according to claim 2, which further comprises one or more kinds of components selected from cooling sensation substances.

9. The sensory stimulant composition according to claim 3, which further comprises one or more kinds of components selected from cooling sensation substances.

* * * * *